United States Patent [19]

Gueyne et al.

[11] Patent Number: 5,037,803

[45] Date of Patent: Aug. 6, 1991

[54] PRODUCT COMPRISING A SILICON ORGANIC COMPOUND COMBINED WITH A COSMETICALLY ACTIVE SUBSTANCE

[76] Inventors: Jean Gueyne; Marie-Christine Seguin, both of Perigord 1, 6 Lacets Saint-Leon, Monte-Carlo, Monaco; Jacques Bondon, 4 Avenue Pasteur, 06240 Beausoleil, France

[21] Appl. No.: 162,875

[22] Filed: Mar. 2, 1988

[30] Foreign Application Priority Data

Mar. 4, 1987 [FR] France ................. 87 02912

[51] Int. Cl.$^5$ .................. A61K 7/02; A61K 7/06; A61K 7/40; A61K 7/48
[52] U.S. Cl. .................................. 514/2; 514/21; 514/63; 514/772; 514/773; 514/263; 530/353; 424/59
[58] Field of Search ................. 424/59; 514/63, 263, 514/772, 773, 2, 21; 530/353

[56] References Cited

U.S. PATENT DOCUMENTS

| | | | |
|---|---|---|---|
| 3,819,825 | 6/1974 | Goodwin | 514/773 |
| 4,347,234 | 8/1982 | Wahlig | 424/426 |
| 4,655,767 | 4/1987 | Woodland | 424/448 |
| 4,659,740 | 4/1987 | Usher | 514/773 |
| 4,663,157 | 5/1987 | Brock | 514/773 |

FOREIGN PATENT DOCUMENTS

| | | | |
|---|---|---|---|
| 0192812 | 11/1983 | Japan | 514/773 |
| 0139308 | 8/1984 | Japan | 514/773 |

OTHER PUBLICATIONS

Abstract of Fr. 1069M, C.A. 59:12911c.
Abstract of Fr. 1,157,158, C.A. 54:18364b.
Abstract of W. German 2,740,801A (counterpart of Fr. 2,369,840), C.A. 89:30796u (1978).
Abstract of Fr. 2,510,407, C.A. 99:58926s (1983).
Abstract of W. German 3,511,135 (counterpart of Fr. 2,561,915), C.A. 104:10408u (1986).
Abstract of W. German 3,346,642 (counterpart of Eur. 156,968), C.A. 103:200704q.

Primary Examiner—Howard E. Schain
Assistant Examiner—Choon Koh
Attorney, Agent, or Firm—Ostrolenk, Faber, Gerb & Soffen

[57] ABSTRACT

Process of preparation of an organo-silicon cosmetic compound having cosmetic and cutaneous resorption activity, derived from the addition or combination or complexing of a silanol with a substance which determines its cosmetic activity and an intracutaneous fixation substance.

21 Claims, No Drawings

PRODUCT COMPRISING A SILICON ORGANIC COMPOUND COMBINED WITH A COSMETICALLY ACTIVE SUBSTANCE

The present invention relates to a process for blocking the penetration of molecular organo-silicon complexes, formulated into cosmetics, at the level of the skin.

It relates particularly to the case where an organic silicon molecule is complexed on the one hand with a substance capable of fixing the compound at the intracutaneous level and on the other hand a substance distinguishing a specificity revealed by the organic silicon in the cosmetic field.

It relates more particularly to organo-silicon cosmetic compounds having cosmetic and cutaneous resorption activity, derived from the addition or combination or complexing of a silanol with a substance which determines its cosmetic activity and an intracutaneous fixing substance.

The biological activity of silanols is well known, however in cosmetics they present the disavantage of being taken up, in most cases, by the microcirculation.

The present invention has the object of the intracutaneous localisation of organo-silicon derivatives or complexes, permitting them to act specifically in response to problems posed in cosmetics.

Because of the invention, this action of silicon is reinforced with a determinism in action limited to the skin. Thus, the process of the invention has for its effect the fixation of the active organo-silicon substance, desired for its concept of treatment at the level of the skin, practically preventing the passage of these cosmetic silanols into the subjacent tissues.

This result is essential in order to comply with cosmetic regulations in force (the law on cosmetics) by adapting the general action of silicon to a particular cosmetic effect. Thus, the advantages mentioned above apply to the new substances, called silicon cosmetics, according to the invention.

Compounds included in by aqueous solutions and/or dispersions of an organo-silicon are known in the art.

A silicon cosmetic according to the invention is constituted by a molecular complex of the hydroxysilane type of the general formula:

$$R_n Si(OR')_m (OR'')_p$$

where

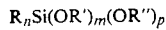

R is an organic substituent without limitation, which can be alkyl or alkenyl, n being a number from 1 to 3;

R' is a specific biologically-active compound

R' thus provides a specificity to the action of the silicon;

the choice of R' is always made in a judicious manner. R' is selected from various chemical substances which alone, in a sufficient quantity or in combination with Si can produce cosmetic or protective effects on the skin, such as slimming, regeneration, stimulation of atonic skins characterised by distended epidermal tissues, loss of colour, brightness and tone, rehydration, re-establishment of the fat content (lubricating action), suntan activation, antierythema action, such as sun erythyma sedation, protection from sun rays protection against UV, anti-blotchiness, thickening of fine skins, anti-stretch-mark treatment, regression of cheloids, anti-wrinkling, delipidic action, antiseborrheic action, treatment of young pimply skins, calming action on the epidermis irritated by shaving or depilation etc., softening action (nails and corns on the feet), deodorising, suppression of epidermal stases of various localisations, rings, bags under the eyes, heavy limbs, softening action on nails, conditioning for the hair, stimulatory action with re-establishing of equilibrium by re-growth of the hair, regression of canities, protection from and reparation after various irritants (wind, cold, UV etc.). In general, the active substances R' are organic compounds which can be carriers, in particular, of one or more alcohol, phenol, acid, amine or aminoacid functions.

Thus substances can be employed such as theophylline and its derivatives, caffeine, acetyltyrosine, glycyrrhysic acid, hydroxyproline, serine and other amino acids, oleic alcohol, parahydroxycinnamic acid, lactic acid, pyrrolidone-carboxylic acid, mannuronic acid, hyaluronic acid and others, these various substances being cited simply in a non-limitative way.

R'' is a dermatophilic molecule which can cause a biochemical or biophysical fixation reaction capable of retaining at different levels in the skin the complex assembly, in order to observe the desired cutaneous action, without all or part of the complex being taken up by the dermal microcirculation. R'' is absorbable by the skin.

R'' complexed is an organic compound functionalized with one or several alcohol, phenol, acid, amine or aminoacid groups. It can be derived from one of the following groups.

1) A macromolecule: in particular nitrogenous and glucidic macromolecules of protein, lipoprotein, nucleoprotein or mucopolysaccharidic type or other mixed macromolecules, comprising chains or groups with chains of another nature.

These macromolecules can be synthetic or natural or they can be controlled hydrolysis products, that is to say in the case of proteins, it can also be a partially hydrolyzed mucopolysaccharide with variable molecular weight, those with shorter chains, polypeptides, cyclopeptides and peptides. By way of example, mention can be made of: egg albumin, blood serum or milk, fibrin, gliadin, glutein, myogen, various bacterial mycelia, elastine and macromolecules resulting from the controlled hydrolysis, casein, collagen, keratin, mucine, salmine, clupein, zein, DNA, RNA, pectic acid, pectins, alginic acid and others, cited here only as non-limitative examples.

This group can also include macromolecules with enzymatic activity, such as desoxyribonuclease, ribonuclease, collagenase, glucoronidase, etc.

2) A polyphenol alone or in the form of a heteroside more or less polycondensed, such as catechin, rutin, rutoside, esculetol and esculoside etc.

3) A sterolic or other non-saponifiable, natural or synthetic, animal or vegetable material, such as the non saponifiable parts of soya, lucerne, cocoa butter, carrot, tomato, nuts, ricin, avocado, such as cholesterol, stigmasterol, sitosterol, carotenoids, xanthophylline, tocopherol, dehydrocholesterols, pyridoxine, thiamine, that is to say all vitamins.

4) A metallic or other oligoelement in the form of a mineral or organic acid and preferably an organic acid of high molecular weight, such as the pyrrolidone-carboxylate of copper, zinc or nickel etc., magnesium or manganese or potassium hyaluronate etc.; haemoglobin, cytochrome, without this list being limitative.

These silanols cosmetics can be obtained by transalkoxylation according to the equilibrium:

$$R_n-Si-(OR')_{(4-n)} + R''OH \Longleftrightarrow$$
$$R_nSi(OR')_{(4-n-1)}(OR'') + R'OH$$

This reaction is carried out in an organic solvent, inert to the siloxane (deprived of the alcohol, primary and secondary amine or acid function).

On the other hand, the products according to the invention can be prepared by complexing an alkylsilanetriol with a mixture of organic compounds R'OH and R''OH, where R' and R'' are the substituents described above. This complexing is already known and can be carried out by mixing solutions of the reactants concerned.

When a complex has first been formed with a compound R', the silicon cosmetic according to the invention can be obtained by transalkoxylation with a molecule R'' if this is in the form R''OH.

The reaction can then be written as:

$$R_nSi(OR')_{(4-n)} + mR''OH \rightarrow R_nSi(OR')_{(4-n-m)} + mR'OH$$

The number n is 1 to 3, m 3 to 1.

The most frequent cases are:
$RSi(OR')_2(OR'')_1$; $RSi(OR')_1(OR'')_2$ and $R_2Si(OR')(OR'')$ Depending upon the nature of the molecules R, R' and R'', in particular depending upon the character and number of the active groups which they carry, the relative proportions of R, R' and R'' in the silicon cosmetic according to the invention can vary widely. In general, but not necessarily, the composition contains 0.2 to 25 atoms of Si per mole of the active cosmetological substance R'; more often, this ratio is 0.3 to 10 atoms of Si per mole of R'.

As regards the molecule R'', the molecular weight of which can vary considerably, its proportion can be selected within the weight limits of 0.2 to 5 parts per part of the substance R' or the R silanol, these amounts not being limitative.

The invention is illustrated non-limitatively by the examples which follow of the manufacture and use of various silicon cosmetics.

EXAMPLES 1 to 6

The specific activity according to different R'' groups is studied. In these silanol cosmetics, the intracutaneous character is due to the molecule R''.

Aqueous solutions of different R silanols and different R's are prepared, all with the same molecule R'', comprising elastine of a molecular weight of about 80,000 of bovine origin, previously rendered soluble in water by the action of an elastese, or by acid or alkaline hydrolysis, without alteration of the physical structure of the elastine. The percentage contents by weight of the composition of each of the constituent R silanols, R' and R'' are given below for Examples 1 to 6.

EXAMPLE 1

| | | |
|---|---|---|
| $R-Si(OH)_{4-n}$ = | methyl-silane-triol $CH_3Si(OH)_3$ | 0.5% |
| R' = | theophylline | 0.45% |

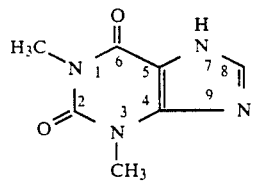

| | | |
|---|---|---|
| R'' = | solubilised, structured elastine (described above) | 0.5% |

In this composition, the molar ratio silanol/R' amounts to 2.13 atoms of Si per mole of theophyllin. The composition has, from the cosmetological standpoint, good slimming properties.

EXAMPLE 2

| | |
|---|---|
| Methyl-silane-triol | 0.50% |
| R' = theophylline acetic acid | 0.59% |

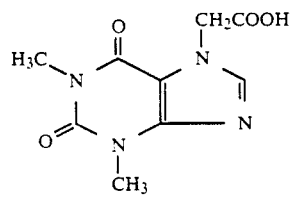

| | |
|---|---|
| R'' = solubilised, structured elastine (as Example 1) | 0.50% |

There are 2.14 atoms of Si per mole of theophylline acetic acid. As in Example 1, this composition exerts a lipolytic activity on the skin.

EXAMPLE 3

| | |
|---|---|
| Dimethyl-silane-diol $(CH_3)_2Si(OH)_2$ | 1.00% |
| R' = glycyrrhizic acid $C_{42}H_{62}O_{16}$ | 0.41% |
| R'' = solubilised structured elastine (as in Example 1) | 0.75% |

The composition contains 25 atoms of Si per mole of the glycyrrhizic acid; its anti-inflammatory and restructuring properties render it useful for use against sunstroke.

EXAMPLE 4

| | |
|---|---|
| Methyl-silane-triol | 0.70% |
| R' = glycine $NH_2CH_2COOH$ | 0.07% |
| R'' = solubilised structured elastine | 0.80% |

There are 8 atoms per mole of glycine.

The composition exerts a very marked scab-forming action.

EXAMPLE 5

| | |
|---|---|
| Methyl-silane-triol | 0.70% |
| R' = sphingomyelin | 1.60% |

-continued

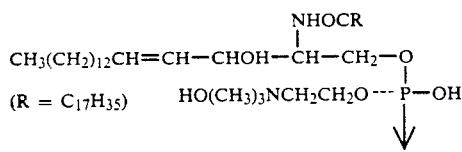

R″ = solubilised structured elastine  0.60%

The ratio Si/R″ is 2.33 atoms Si per mole of sphingomyeline. The composition has anti-pellicular properties.

EXAMPLE 6

| Dimethyl-silane-diol (CH₃)₂Si(OH)₂ | 0.93% |
|---|---|
| R′ = acetyl-tyrosine acid | 2.19% |
| R″ = solubilised structured elastine | 0.60% |

The solution contains 1 atom Si per mole of acetyl-tyrosine acid. It is active at 3.5% as a suntan activator.

EXAMPLES 7 TO 12

The specific activity is the same for each of these silanol cosmetics, because the same R′ is used while varying R″ with respect to the various groups of organic compounds cited above. These silanol cosmetics are prepared according to the invention as in Examples 1 to 6. The molecule R′ is acetyltyrosine; the molecule R″ is constituted by collagen, esculoside, cholesterol, sphingomyelin, copper pyrrolidone carboxylate and tocopherol.

| EXAMPLE | Si = 0.15%<br>R = 0.5% | R′ = 0.25 | R″ = 0.1 |
|---|---|---|---|
| 7 | CH₃Si(OH)₃ | | Esculoside<br>Polyphenol |
| 8 | " | | Copper pyrrolidone<br>carboxylate |
| 9 | (CH₃)₂Si(OH)₂ | | Collagen |
| 10 | CH₃Si(OH)₃ | Acetyl<br>tyrosine<br>acid | Sphingomyelin |
| 11 | (CH₃)₂Si(OH)₂ | | Oleic Alcohol |
| 12 | CH₃Si(OH)₃ | | Cholesterol |

The silicon is metered into the skin of rats used for the experimentation at 24 hours and 10 days after applications of a placebo gel, control group, an RR′ gel, group I, and an RR′R″ gel, group II, such as defined above for comparative studies. In all the cases, 1 g of the gel is applied to 2 cm² of skin, for groups I and II, which corresponds to 500 microgrammes of Si per application. With the placebo control group, the Si content in the rat skin is determined, namely 114±25 microgrammes per g.

TABLE

| Si content in control group | Derivatives | Dosage of Si in the skin in μg/g | | | | |
|---|---|---|---|---|---|---|
| | | Quantity of Si given in Group I | Increase in Si or Si retained in the skin - Group I | | Quantity of Si given in Group II | Increase in Si or Si retained in the skin - Group II |
| 114 ± 25 | 7 | 489 ± 35 | 375 ± 60 | 75% | 680 ± 45 | 566 ± 70 113% |
| | 8 | 474 ± 23 | 360 ± 48 | 72% | 595 ± 34 | 480 ± 59 96% |
| | 9 | 480 ± 36 | 366 ± 61 | 73% | 626 ± 19 | 511 ± 44 102% |
| | 10 | 465 ± 43 | 351 ± 68 | 70% | 609 ± 38 | 495 ± 63 99% |
| | 11 | 471 ± 52 | 357 ± 77 | 71% | 672 ± 15 | 558 ± 40 112% |
| | 12 | 492 ± 26 | 378 ± 51 | 76% | 612 ± 25 | 498 ± 50 99% |

This shows that the average quantity of Si retained in the skin in the case of the compounds according to the invention, RR′R″, are about 100%, taking into account the types of ranges, while those corresponding to the complex RR′ appear to show a loss of 40% of the Si.

EXAMPLE 13

A composition for a skin regenerative cream is prepared as follows.

| Methyl-silane-triol | 1% |
|---|---|
| R′ = mannuronic acid | 0.625% |
| R″ = mucopolysaccharide | 0.5% |

Results of application of this composition are given below in Example 19.

EXAMPLE 14

Acetyl-tyrosine acid, a substance capable of exerting a cosmetological action, has been employed in the form of the following composition:

| Dimethyl-silane-diol (CH₃)₂Si(OH)₂ | 0.5% |
|---|---|
| R′ = acetyl-tyrosine acid | 0.703% |

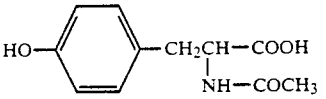

| R″ = polypeptidic chain of collagen.<br>molecular weight >40000 | 1% |
|---|---|

The ratio Si/R′ is 1.59 atoms Si/mole acetyl/tyrosine acid. The composition constitutes a good suntanning activator.

EXAMPLE 14 bis

| R = CH₃Si(OH)₃ | R′ = elastine | R″ = sorbitol |
|---|---|---|

EXAMPLE 15

In this preparation, R″ which fixes the functionalised silanol into the skin, is constituted by nucleoproteins: The composition comprises:

| Methyl-silane-triol | 0.5% |
|---|---|
| R′ = lactic acid CH₃CHOHCOOH | 0.489% |
| R″ = nucleoproteins | 1.5% |

The molar ration Si/lactic acid=0.98. The composition exerts a moisturising action on the skin.

USES OF THE COMPOSITIONS ACCORDING TO THE INVENTION EXAMPLE 16

Example of the use of the silanol cosmetic of Example 2 in a water-dispersable slimming cream. The cream containing 5% of the silanol cosmetic is applied daily to adipose zones of 10 patients in 50 massage sessions The results obtained comparatively with a placebo and with a 6% solution of acetic-theophylline (which gives a ratio of 1 to 10) give rise to the following averages:

|  | Silanol cosmetic at 5% | Placebo | Theophylline Acetic Acid 6% |
|---|---|---|---|
| Waist | −3.5 = 5% | −0.4 | −1.2 = 1.7% |
| Hips | −4.4 = 4.9% | −0.6 | −1 = 1.1% |
| Thighs | −1.7 = 3.8% | +0.1 | −0.2 = 0.4% |
| Knees | −0.6 | 0 | 0 = 0 |

It follows that the silicon cosmetic according to the invention has a strong slimming action. On the other hand, 5 human adipocyte cultures were effected, carried out on marked fatty acids:
  (A) Control culture without additive;
  (B) Culture containing 1 mg per ml of the culture of a solution of 0.45% of theophylline;
  (C) Culture containing 1 mg per ml of the culture of a solution of 0.59% of theophylline acetic acid;
  (D) Culture containing 1 mg per ml of the culture of a silanol cosmetic of Example 1;
  (E) Culture containing 1 mg per ml of the culture of the silanol cosmetic in Example 2.

The lipolytic activity has been found to double in the cultures (D) and (E) with respect to the control (A), while there is only an increase of about 20% for the cultures (B) and (C). The silanol cosmetic (D) and (E) has thus exerted a positive influence.

EXAMPLE 17

Use of the composition of Example 3 against solar erythema.

A gelified lotion containing 6% of the composition of Example 3 is applied in several cases of "sun-stroke," in parallel with a similar lotion of 6% of a solution of 0.75% glycyrrhyzic acid, with a silanol or R". This confirmed that the silanol cosmetic of Example 3 caused rapid disappearance of the pain and the intensity of the reddening and avoided all discoloration (desquamation), if it was applied for 3 days. In the absence of the silanol cosmetic, the intensity of the erythema was measured obtaining the following results.

|  | Silanol cosmetic | Glycyrrhyzic acid | Placebo |
|---|---|---|---|
| Pain | nil | quite strong without heat | strong with heat |
| Erythematons intensity | 1 | 3.5 | 5 |
| Desquamation | nil | weak | considerable |

EXAMPLE 18

Use of the silanol cosmetic of Example 14 bis, which shows a regenerative action.

After making an incision in the skin on the back of a rat, scab formation was allowed to occur for seven days and then the product was applied, together with a placebo, over 17 days. The histological study of the scab allowed a re-structured epidermis to be observed, without nodules, comparable with the healthy epidermis; the sub-epidermal zone was regenerated, in comparison with a placebo control, where scab nodules appeared with a hyperplastic epidermis. The subjacent tissue was still disorganised and disoriented.

EXAMPLE 19

Use of the composition of Example 13.

A cosmetic emulsion of 6% of the composition was used as a regenerative cream. Observations were carried out on aged females after application for two months. Appreciation of the efficiency of the product was carried out by elasticity tests, that is comparative measurement of the retractability of the skin after subjecting it to a predetermined force. The improvement in the retractability before and after treatment was shown in a significant fashion. On the other hand, it was noted that 6 hours after application of the composition, 96% of the silanol used remained in the skin; by contrast, only 75% remained when the composition utilized did not contain the mucopolysaccharide. This well characterises its role in fixation of the active substance in the skin.

EXAMPLE 20

Use of the silanol cosmetic of Example 14 as a suntanning activator.

In order to obtain an excellent suntanning activator, a cosmetic preparation of 7% of the solution according to example 14 was used. Comparative tests were carried out on the same subject of skin type 1, by exposure to UVA and UV B. Sunburn was observed on the surface of the skin treated, while on the exposed but non-treated skin there was an erythema of index 2. On skin of type 2, an intense sunburn was observed on the treated surface, while the exposed but not previously treated skin was slightly reddened. More transient result were observed when the composition did not contain collagenic polypeptides. This shows the interest in the suntanning activator of the particular composition according to Example 14, for skins of the types 1 and 2 subjected to intensive exposures of short duration.

EXAMPLE 21

Use of the present invention for a hair conditioner of the following composition:

| Methylsilane-triol | 0.1 to 5% |
|---|---|
| Solubilised and structured elastine | 1 to 10% |
| Fatty acid polyester | 0.1 to 5% |

Variation of the quantities indicated allowed the conditioning qualtiy for hair or a lacquer to be modified, that is the degrees of fixation on fly-away hair of shiny appearance. The solution can be aqueous or alcoholic and allows a biological hair lacquer or conditioner to be obtained yielding better growth.

We claim:

1. A cosmetic product which comprises an aqueous solution of (a) silanol, (b) a cosmetically active substance and (c) a material which fixes the silanol and cosmetically active substance in the skin, said material is a protide.

2. The product of claim 1, wherein the protide is a lipoprotide or a nucleoprotein.

3. Product according to claim 1, in which the silanol is of the formula $R_xSi(OM)_{(4-x)}$ where R is an alkyl, alkenyl or aryl, x is a number of 1 to 3 and M is an atom of alkali metal or hydrogen.

4. Product according to claim 1, wherein the cosmetically active substance is an agent of slimming, skin regeneration, stimulation of atonic skins, brightening, rehydration, lubricating, suntan activation, protection against UV, anti-blotchiness, thickening of fine skins, antistretch mark treatment, regression of cheloids, antiwrinkling, delipidic action, antiseborrheic action, calming and softening action, deodorizing, suppressing epidermal stases, softening nails, conditioning for hairs, stimulating hair growth, regression of canities and protection from atmospheric agents.

5. Product according to claim 4, wherein said agent is theophylline, a theophylline derivative, acetyl tyrosine acid, glycyrrhizic acid, glycine, lactic acid, hydroxyproline, sphingomyeline, mannuronic acid or a fatty alcohol.

6. Product according to claim 4, wherein the material which fixes the silanol and the cosmetically active substance in the skin is a natural protein which has retained its natural structure.

7. Product according to claim 1, in which said material is a polyphenol alone or in the form of heteroside, or it is a sterolic compound.

8. Product according to claim 1, in which said material is a metallic oligoelement.

9. Product according to claim 1, which bears 0.2 to 25 Si atoms per mole of said cosmetically active substance and 0.2 to 5 weight part of said material fixing it in the skin per each weight part of the cosmetically active substance.

10. Product according to claim 4, wherein the cosmetically active substance is a rehydratant, an antiseborrheic agent or nail softener.

11. Product according to claim 1, wherein the cosmetically active substance is a calming anti-inflammatory, a cutaneous protector, a sun erythema sedative, a post depilatory, a deodorant, a protector from sun rays, an anti-erythema or a suntan activator.

12. Product according to claim 1, wherein the cosmetically active substance is as a detoxicant of skin by eliminating deposits and stasis.

13. Product according to claim 1, wherein the cosmetically active substance is a hair conditioner.

14. Product according to claim 6, wherein the material which fixes is partially hydrolyzed elastin.

15. Product according to claim 4, wherein said agent is theophylline, a theophylline derivative, acetyl tyrosine acid, glycyrrhizic acid, glycine, lactic acid, hydroxyproline, sphingomyeline, mannuronic acid or a fatty alcohol.

16. Product according to claim 15, wherein the material which fixes the silanol and the cosmetically active substance in the skin is a natural protein which has retained its natural structure.

17. Product according to claim 16, wherein the silanol is methyl silane triol, the active substance is theophylline and the material which fixes the silanol and theophylline in the skin is partially hydrolyzed elastin.

18. Product according to claim 1 in which the silanol is methyl silane triol or dimethyl silane diol.

19. Product according to claim 1 in which the amount of silanol is 0.1 to 5%, the amount of cosmetically active substance is 0.1 to 5% and the amount of said material is 0.1 to 10%.

20. Product according to claim 1 wherein the aqueous solution contains 0.5 to 0.95% methyl silane triol or dimethyl silane diol, 0.25 to 2.19% of theophylline, theophylline acetic acid or acetyl tyrosine, and 0.5 to 1% of water solubilized elastin or collagen.

21. A cosmetic product according to claim 1 consisting essentially of 0.1 to 5% of a silanol of the formula $R_xSi(OM)_{(4-x)}$ in which R is an alkyl, alkenyl or aryl, x is a number from 1 to 3 and M is an atom of alkali metal or hydrogen, 0.1 to 5% of said cosmetically active substance and 0.1 to 10% of said material which fixes the silanol and cosmetically active substance in the skin.

* * * * *